United States Patent
Widlund et al.

[19]

[11] Patent Number: 5,901,419
[45] Date of Patent: May 11, 1999

[54] FASTENER MEANS FOR DISPOSABLE ABSORBENT ARTICLES

[75] Inventors: Urban Widlund, Mölnlycke; Anna Karin Jönbrink, Lerum, both of Sweden

[73] Assignee: SCA Hygiene Products AB, Goteborg, Sweden

[21] Appl. No.: 08/973,421

[22] PCT Filed: Jun. 27, 1996

[86] PCT No.: PCT/SE96/00854

§ 371 Date: Jan. 5, 1998

§ 102(e) Date: Jan. 5, 1998

[87] PCT Pub. No.: WO97/02798

PCT Pub. Date: Jan. 30, 1997

[30] Foreign Application Priority Data

Jul. 7, 1995 [SE] Sweden ................................. 9502493

[51] Int. Cl.$^6$ .............................. A44B 17/00; A61F 13/00
[52] U.S. Cl. ............................... 24/304; 24/442; 24/300; 24/301
[58] Field of Search .............................. 24/304, 301, 300, 24/114.6, 712, 712.1, 715.3, DIG. 11

[56] References Cited

U.S. PATENT DOCUMENTS

| | | | |
|---|---|---|---|
| 481,425 | 8/1892 | Robinson | 24/300 |
| 1,153,334 | 9/1915 | Oswald | 24/300 |
| 2,679,671 | 6/1954 | Garber, Jr. | 24/301 |
| 3,403,427 | 10/1968 | Asseo et al. | 24/304 |
| 3,677,250 | 7/1972 | Thomas | 24/DIG. 11 |
| 3,808,648 | 5/1974 | Billarant et al. | 24/442 |
| 3,828,365 | 8/1974 | Berger . | |
| 4,894,060 | 1/1990 | Nestegard | 24/442 |
| 5,554,146 | 9/1996 | Niederhofer et al. | 24/442 |

FOREIGN PATENT DOCUMENTS

| | | |
|---|---|---|
| 69136 | 10/1958 | France . |
| 170239 | 2/1960 | Sweden . |
| 701904 | 1/1954 | United Kingdom . |
| 810626 | 3/1959 | United Kingdom . |

*Primary Examiner*—Victor N. Sakran
*Attorney, Agent, or Firm*—Burns, Doane, Swecker & Mathis LLP

[57] ABSTRACT

A fastener for absorbent articles, such as pants-type diapers or incontinence guards, includes a first fastener element and a second fastener element (1, 4) which are intended to be hooked together when donning the article. The first element (1) includes an elastic structure (2) which includes openings (6) and is so constructed that the openings (6) will widen when the elastic structure (2) is stretched and closed together when the elastic structure contracts. The second element (4) includes hook devices (5). When the elastic structure (2) is sufficiently stretched, the hook devices (5) can be inserted into the widened openings (6), wherein subsequent contraction of the elastic structure (2) will cause the first and the second elements (1, 4) to be joined together with the opening (6) surrounding the hook device (5).

12 Claims, 5 Drawing Sheets

FASTENER MEANS FOR DISPOSABLE ABSORBENT ARTICLES

TECHNICAL FIELD

The present invention relates to fastener means for absorbent articles, such as pants-type diapers, diapers, incontinence guards or like articles, said fastener means comprising a first and a second fastener element which are intended to be hooked together when donning the article.

The invention can also be applied with pants that are intended to support an absorbent insert.

BACKGROUND OF THE INVENTION

The present invention relates to fastener means for disposable absorbent articles, such as diapers, pants-type diapers, incontinence guards or the like. Disposable absorbent articles of this kind are normally comprised of a liquid-permeable outer sheet, a liquid-impermeable backing sheet and an absorbent core enclosed therebetween. The outer sheet and the backing sheet are normally joined together outside the edges of the absorbent core and together form a casing or envelope. The outer sheet may have the form of elastic pants having a waist opening and two leg openings and including an absorbent core and a non-elastic backing sheet. The article is normally elongated and has a front waist region, a rear waist region and a narrower crotch region situated therebetween. The article also includes different elastic devices, mainly at the side edges of the crotch region and at the end edges of the waist regions, the purpose of these devices being to improve the fit of the article around the leg openings and around the waist respectively.

The article is secured around the waist of the wearer with the aid of fastener means provided at the side edges of the waist regions. These fastener means may, for instance, have the form of adhesive tabs mounted on the side edges of the rear waist region and fastened to the front waist region of the article when the article is donned. The fastener means may alternatively have the form of mechanical devices, such as touch-and-close fasteners, e.g. Velcro® fasteners where one pile surface is comprised of hooks and is fastened to an adapted pile surface comprised of loops. The fastener means may also comprise press studs, other forms of studs, or buttons.

The aforesaid conventional fastener means are encumbered with many drawbacks.

Conventional fastener means are designed to close the article around the waist of the wearer. Seen generally, typical fastener means are comprised of a receiving element and an adhering element. The receiving element is mounted on each side edge of one waist region, normally the front waist region, and the adhering element is mounted on each side edge of the opposing waist region. The elements are fastened together and mutually connect the waist regions. When putting-on the article, the adhering element is pressed against the receiving element so that the elements stick together. The pressure is applied at right angles to the plane of the waist region, i.e. against the wearer's stomach.

One advantage afforded by the inventive fastener means is that the article is closed by deformation of one element parallel with the plane of the waist regions, without subjecting the wearer's body to any appreciable pressure.

Conventional fastener means are subjected to large shear forces in use, as a result of wearer body movement. The adhering element is normally fastened to the receiving element while the wearer stands in an upright or lies in a recumbent position. In these positions, both waist regions of the article are situated at generally the same height around the wearer's waist. The receiving element is most often mounted on the front waist-region of the article and the article is therewith closed and fastened in the vicinity of the wearer's stomach. When the wearer is seated, the front waist-region tends to move down and the rear waist-region tends to move up, which is a natural consequence of bending the body. This results in the occurrence of large shear forces between the adhering element and the receiving element. An attempt has been made to solve this problem, by providing the fastener elements with larger contact surfaces.

A clear advantage afforded by the inventive fastener means is that it is deformable even in a vertical direction and is able to follow the movements of the wearer, by contracting and stretching with no impairment to its fastening properties.

Another drawback with conventional fastener means is that the wearer is able to release the fastener easily at times which might prove hazardous, by simply tearing the fastener elements apart. This drawback is also eliminated by the inventive fastener means. In order to release an inventive fastener means, it is necessary to subject one fastener element to two forces in two different directions simultaneously, the first direction being parallel with the fastener element and the other direction being away from the wearer's body.

Another drawback with conventional fastener means, and then with adhesive tabs in particular, is that they lose some of their fastening ability when fastened and released repeatedly, or when coming into contact with skin cream or talcum powder, for instance. Mechanical fastener means are also difficult to locate on the article so as to obtain an optimal fit with regard to wearers of varying anatomies. In order to circumvent this problem, it is often necessary to provide the article with an otherwise unnecessarily wide receiving element, therewith adding considerable cost to the manufacture of the article. Excessively wide touch-and-close fastener surfaces also impair wearer comfort, because they are stiff, difficult to bend, inelastic, and also fasten readily to the wearer's and the nurse's clothing.

It is therefore apparent that the fastener means of absorbent articles, such as pants-type diapers, diapers, incontinence guards and like articles are in need of significant improvement.

The present invention eliminates all of the aforesaid drawbacks in an effective and efficient manner.

OBJECT OF THE INVENTION AND ITS MAIN CHARACTERISTIC FEATURES

An inventive fastener means is characterized in that the first fastener element comprises at least one elastic part which includes at least one opening and which is constructed so that the opening will widen when stretching the elastic part and draw together or close when the elastic part retracts; in that the second fastener element includes at least one hook device; in that with the elastic part adequately stretched, the hook device can be inserted in the therewith widened opening, wherein subsequent spring-back or contraction of the elastic part causes the first and the second fastener elements to couple together with the opening disposed around the hook device.

According to one embodiment of the present invention, the first fastener element includes a sheet of pliable material. The elastic part is comprised of an elastic structure disposed on the pliable sheet. The opening has the form of a continuous or cut or slit or intermittent cuts or slits in the pliable sheet. The elastic structure can be stretched at least transversely to the direction of the slit or slits and at least a part of the elastic structure extends transversely to said slit.

The elastic structure is comprised of at least one elastic loop or at least one elastic net, having a number of generally parallel segments which can be stretched at least transversely to the direction of the slit and which extend transversely thereto.

According to one embodiment of the present invention, the first fastener element is placed in the immediate vicinity of or forms a part of one waist region of the article, preferably the rear waist-region. The article includes a plurality of mutually parallel elastic threads which are tensioned transversely along the whole of the rear waist-region. The first fastener element of the fastener means is obtained by providing narrow slits between and perpendicular to the threads, at the side edges of the rear waist-region. As the rear waist-region is stretched, the slits are widened in the transverse direction of the article and are able to embrace hook devices configured to this end, said devices being disposed on the corresponding side edge of the front waist-region. As the rear waist-region is relaxed, the hook devices will lock into respective slits as the slits close as a result thereof.

BRIEF DESCRIPTION OF THE DRAWINGS

FIG. 1a illustrates the fastening means with the fastener elements not connected. The first element is stretched and the opening widened. The arrows indicate the applied stretching forces.

FIG. 1b shows the fastener means with the elements connected. The first element springs back or contracts and the opening closes around the hook devices. The arrows indicate the spring-back or contraction forces.

FIG. 2a shows the diaper in a flat, extended state with the rear side of the diaper facing towards the viewer. A first fastener element is provided at each side edge of the rear waist-region. The hook devices are mounted on each side edge of the front waist-region. The elastic structure is comprised of an elastic net.

FIG. 2b illustrates another embodiment in which a first fastener element is mounted along the rear waist-region and forms a waist band or belt. The belt includes a slit at each end thereof. The hook devices are mounted at each side edge of the front waist-region. The elastic structure is comprised of an elastic net which extends transversely across the whole of the waist belt.

FIG. 2c illustrates the same diaper as that illustrated in FIG. 2b when donned around the wearer's waist (not shown), with the fastener means still not fastened. The first fastener element is shown in a stretched state.

FIG. 2d illustrates the same diaper as that shown in FIG. 2b in use, with the fastener means fastened. The first element is shown in its relaxed, contracted state.

FIGS. 3 to 5 illustrate three different embodiments of the first fastener element and show the elements in a) a stretched state and b) in a relaxed, contracted state.

FIG. 3 (3a and 3b) illustrates a first element where the elastic structure is comprised of an elastic loop and the opening has the form of a continuous slit.

FIG. 4 (4a and 4b) illustrates a first element where the elastic structure is comprised of an elastic loop and the opening has the form of intermittent slits.

FIG. 5 (5a, 5b, 5c and 5d) illustrate a first element where the elastic structure has the form of an elastic net.

FIGS. 6 shows the entire fastener means from above, said means including a first fastener element according to FIG. 3 and associated hook devices.

DESCRIPTION OF EXEMPLIFYING EMBODIMENTS

The invention will now be described in more detail with reference to the drawings.

The fastener means illustrated in FIG. 1 is comprised of two mutually adapted elements 1, 4 which can be fastened together and released any number of times without impairing their fastening ability. Seen generally, the first element 1 is characterized by its elastic properties and the second element 4 by the hook devices 5.

Fastener means construction

The first element 1 is comprised of a generally flat, rectangular blank made of pliable material, for instance nonwoven material.

The elastic part is comprised of an elastic structure 2 which is mounted on the blank and which can stretch and contract in at least one direction in the plane of the blank, the stretch direction, as shown by the arrows 1a and 1b respectively. The blank includes at least one opening or one discontinuity in the material. In the case of the embodiment illustrated in FIG. 1, the first fastener element 1 includes an elongated slit 3 which extends continuously transversely to the stretch direction and divides the blank into two separate parts 11 and 12.

Figures 1A, 1B:
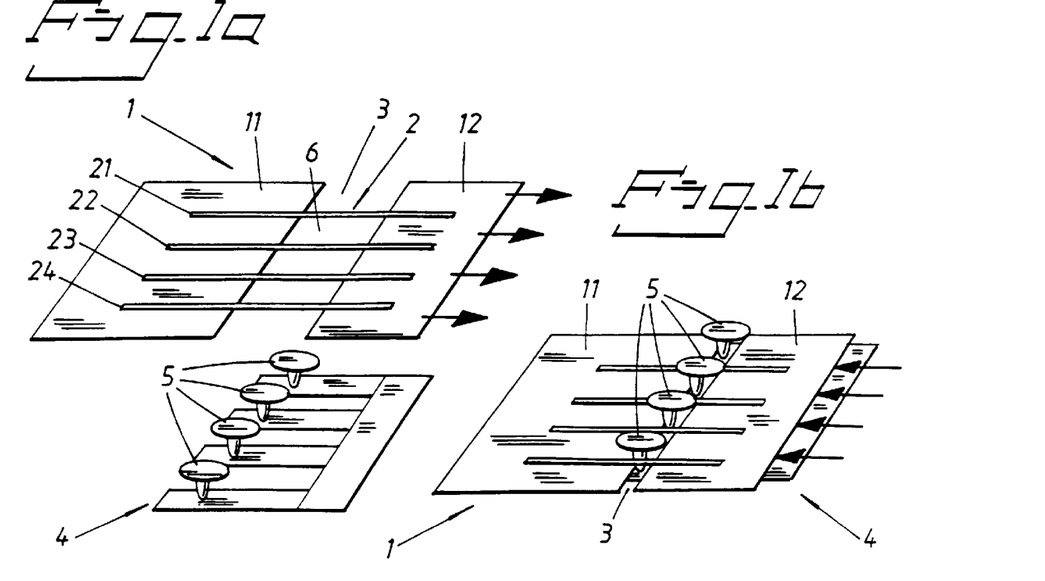
FIGS. 1a and 1b are schematic perspective views of one embodiment of an inventive fastener means, and illustrates the functioning of said means.
Figure 9:
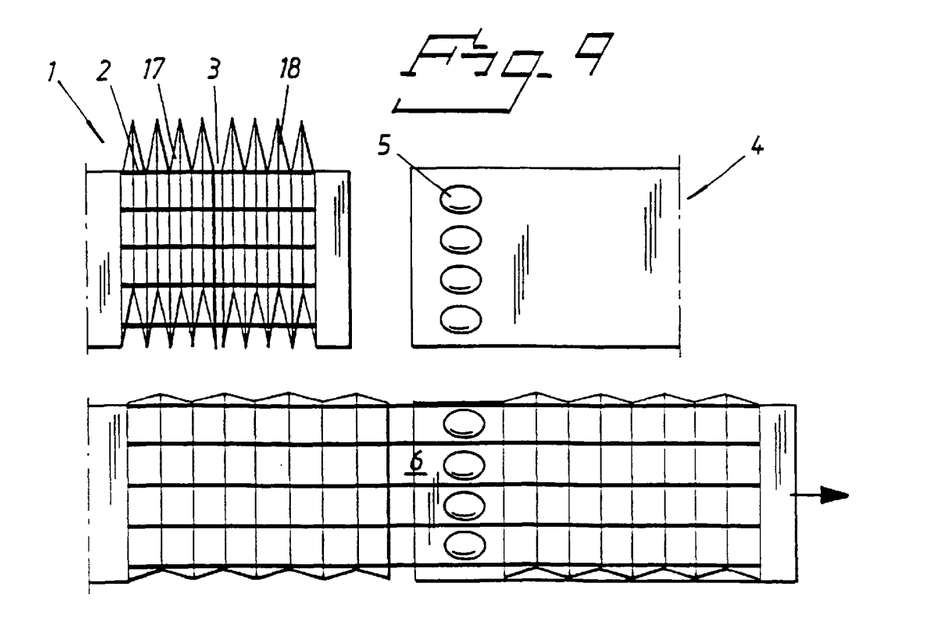
FIG. 9 illustrates a further embodiment of an inventive fastener means, wherein which a pre-tensioned elastic structure is mounted on a blank. The structure is mounted intermittently on the blank and generates pleats or puckers in the blank when no load acts thereon, and smoothens out the blank when stretched.

The elastic structure 2 is comprised of a plurality of mutually parallel elastic devices 21–24, such as threads or bands, which extend transversely to the slit 3 and join the different blank-parts 11, 12 together. The elastic devices 21–24 are preferably mounted on the blank in a stretched state. The blank is puckered together when the elastic devices 21–24 are in their relaxed or contracted state. The puckers are formed transversely to the stretch direction (shown in FIG. 9 but not in FIG. 1). When the elastic devices 21–24 are in their contracted state, the slit 3 will be closed and the two parts 11, 12 of the blank will lie close to one another, as shown in FIG. 1b. The elastic structure 2 may alternatively be mounted on the blank in a relaxed state. In this case, it is necessary for the slit 3 to have a given width also in the relaxed state, since only that part of the structure 2 which extends over the slit 3 can stretch and contract. The first fastener element 1 of the fastener means shown in FIG. 1 is comprised of two parts 11, 12. The part 11 is attached to the article (not shown) and the part 12 is free.

The second fastener element 4 of the fastener means shown in FIG. 1 is comprised of a flat, rectangular blank of pliable material, for instance nonwoven material. In the FIG. 1 embodiment, the second fastener element 4 includes a plurality of upstanding, mushroom-like hook devices 5 which are preferably made of a rigid material. The second fastener element 4 of the FIG. 1 embodiment is attached to the article (not shown).

When closing the fastening means, the free part 12 and the fastener element 1 are pulled out in the stretch direction, as shown by the arrows in FIG. 1a. This widens the slit 3 in the stretch direction, so as to form a gap. A plurality of square openings 6 are created in the gap between said parts 11, 12, in the intervals between the stretched elastic devices. The first element 1 is then brought together with the second element 4, so that each of the hook devices 5 will be enclosed in a respective opening 6. The free part 12 of the first element 1 is then released, whereupon the elastic structure 2 contracts and strives to re-close the slit 3. The openings 6 are therewith drawn together around at least part of the stem of the hook devices 5, so as to secure the fastener means.

POSITIONING OF THE FASTENER MEANS ON THE ARTICLE

Figure 2A:
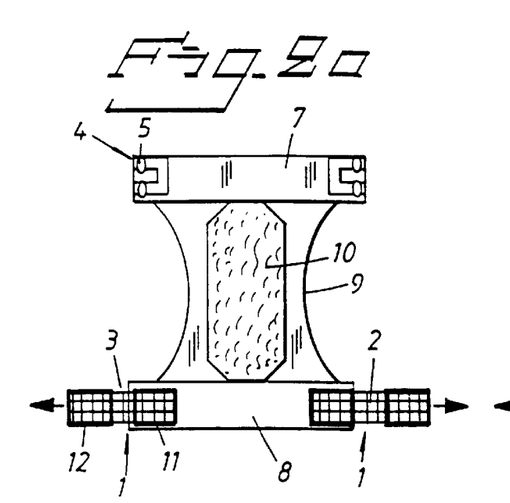
FIGS. 2a–2d illustrate a diaper that includes an inventive fastener means.

FIG. 2a illustrates a diaper provided with an inventive fastener means. The diaper is shown in a flat state, prior to being donned. FIG. 2a shows the rear side of the diaper (i.e. the side which lies distal to the wearer in use). The diaper has a generally rectangular, elongated shape and includes a front waist-region 7, a rear waist-region 8 and a narrowing crotch region 9 situated therebetween, the major part of the absorbent core 10 being located in the crotch region. The rear waist-region 8 has an elongated, rectangular shape and extends along the rear end-edge of the diaper, transversely to the longitudinal axis thereof. A first fastener element of the fastener means is mounted at each end of the rear waist-region.

The front waist-region 7 has an elongated, rectangular shape and extends along the front end-edge of the diaper, transversely to the longitudinal axis thereof. A second fastener element 4 of said fastener means is mounted at each end of the front waist-region.

The first element 1 is comprised of a generally flat, rectangular blank made of pliable material, for instance nonwoven material.

The blank includes an elastic structure 2 which is able to stretch and contract in at least one direction in the plane of the blank, referred to as the stretch direction, as indicated by the arrows in FIG. 2a.

The first fastener element 1 of the fastener means shown in FIG. 2 includes an elongated slit 3 which extends continuously transversely to the stretch direction and divides the blank into two separate parts 11 and 12.

The elastic structure 2 has the form of an elastic net which extends transversely to the slit 3 and unites the different blank-parts 11, 12.

The second element 4 of the fastener means shown in FIG. 2 has at least one hook device 5.

Figure 2B:
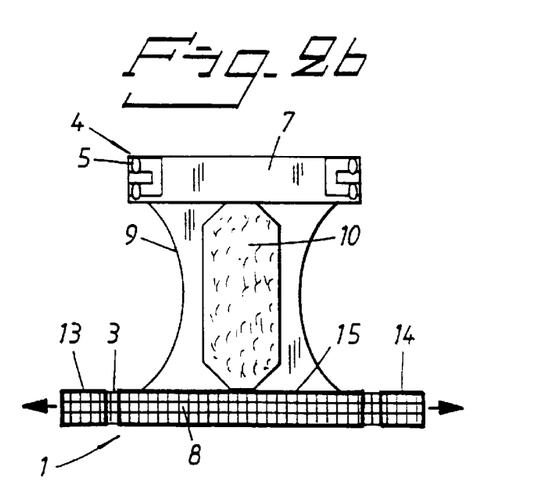

FIG. 2b shows a diaper of the same type as that shown in FIG. 2a, but provided with a different embodiment of an inventive fastener means. A first element 1 of the fastener means according to FIG. 2 extends transversely across the diaper, along the rear waist-region 8.

The element 1 is comprised of two end-parts 13, 14 and an intermediate centre part 15. The centre part 15 is joined to the rear waist-region and is connected to both end-parts 13, 14 by an elastic structure 2 (in the illustrated case an elastic net) which extends along the element.

The centre part 15 may consist in the rear waist-region 8 or in a part of said region. That part of the elastic structure 2 which extends in the centre part 15 also serves as an elastic waist belt or waistband, to improve the fit of the article around the wearer's waist.

Similar to the free part 12 in FIGS. 1a, 1b and 2a, the end-parts 13, 14 consist in a flat, rectangular pliable blank in which the structure 2 is mounted.

A cut or slit 3 is formed in the boundary line between the centre part 15 and each end-part 13, 14, in a manner similar to that shown in FIG. 2a. When the elastic net 2 is in its contracted or relaxed state, the slits 3 are closed and the parts 13, 14, 15 will be contiguous with one another.

As the element 1 is stretched, the slit 3 is widened in the stretch direction, as indicated by the arrows, to form a gap. As the meshes of the net 2 widen in the stretch direction, a plurality of square openings 6 are formed in the gap between the end-parts 13, 14 and the centre part 15.

Figure 2C:
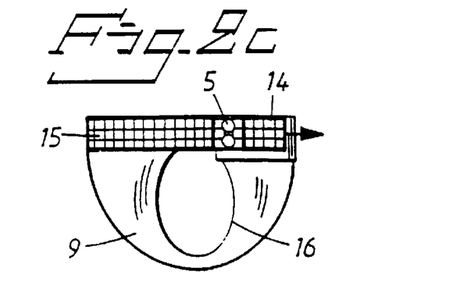
Figure 2D:
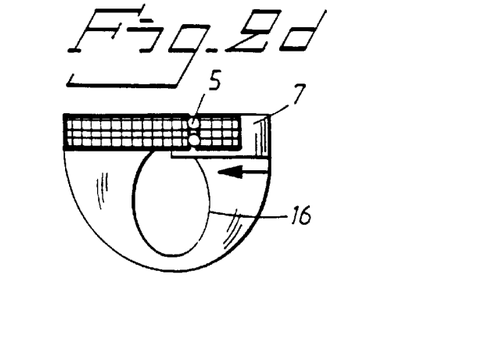

FIGS. 2c and 2d are side views of the diaper shown in FIG. 2b, and show one side-edge of the rear waist-region 8 connected to a corresponding side-edge of the front waist-region 7. The leg openings 16 of the diaper are formed in this way.

FIG. 2c shows the first element 1 in a stretched state, in which the end-part 14 is drawn out in the stretch direction as shown by the arrow. The slit 3 is widened and a gap is formed over the hook devices 5.

FIG. 2d shows the fastener means in its fastening state. The slit 3 will close when the end-part 14 is released, wherewith the meshes in the net 2 will be drawn together around the hook devices 5.

The design of the first fastener element 1

Figure 3A:
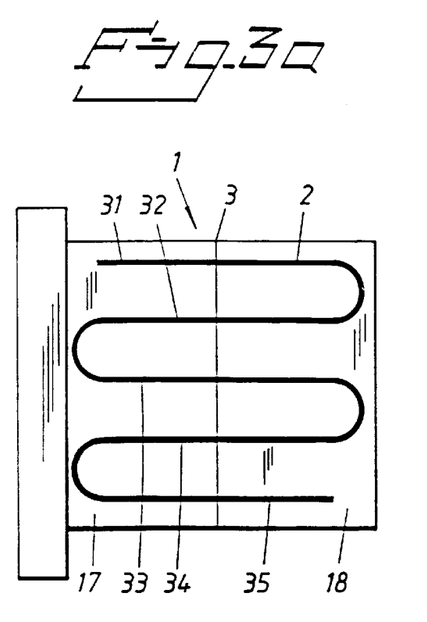
Figure 3B:
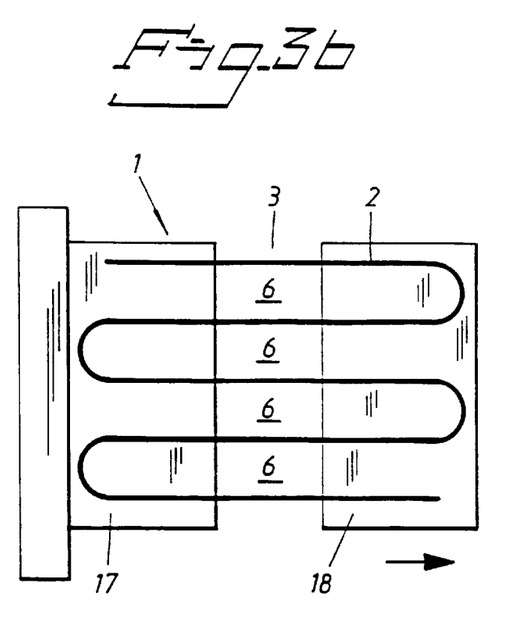

In the case of one embodiment of the first element 1, such as the embodiment shown in FIGS. 3a, 3b, the element 1 is comprised of a nonwoven rectangular blank which has a fixed end 17 and a free end 18.

The fixed end 17 can be presumed to be attached to the article, for instance in its rear waist-region, in accordance with FIG. 2a. The fixed end 17 may also represent the centre part 15 of the element, in accordance with FIG. 2b.

FIG. 3a shows the fastener element when not subjected to load.

FIG. 3b shows the same element in a stretched state. The blank is separated along the whole of its width, or along the greatest part of its width, by means of a slit 3.

The elastic structure is comprised of a loop 2 of elastic thread which includes a number of mutually parallel segments 31, 35 that extend across the slit 3 at right angles thereto. The elastic loop 2 can be stretched and relaxed in the direction of the parallel segments. The loop 2 is preferably mounted on the blank with the loop in a stretched state. The blank is compressed when no load acts thereon, i.e. when the loop 2 is in a contracted or relaxed state, therewith keeping the slit 3 closed. As the free end 18 of the blank is extended in the stretch direction, as shown in FIG. 3b, the loop 2 will stretch and the slit 3 widen in the direction of the stretching force, so as to form a gap in the blank. Square openings 6 are therewith formed in the interval between the parallel loop-segments 31–35 in said gap. When the stretching force is released, the loop 2 will contract to its relaxed state while closing the opening 6.

The first fastener element 1 can be constructed in many different ways with regard to the following aspects:

Firstly, the elastic structure may be comprised of elastic material arranged in different configurations, such as in the form of loops, parallel threads, nets, curves, or may comprise a perforated sheet of elastic or resilient material, such as foam, plastic, elastic nonwoven material or like materials.

Secondly, the elastic structure 2 may be mounted on the blank in different ways. It can be mounted in a pre-stretched state, extended in the stretch direction and also in other directions. In such cases, the structure 2 is affixed to the blank, for instance glued, ultrasound-welded or heat-sealed thereto, and is then allowed to relax or contract so as to pucker the blank. The blank will smooth out as the structure is stretched. See in particular FIG. 9, which shows the blank in the first element is pleated or puckered when no load acts thereon, by virtue of the structure being attached to the pliable material in a punctiform manner.

The elastic structure 2 may also be mounted in a relaxed state. In this case, at least part of the structure will be affixed to the blank. The blank may consist in two mutually overlapping parts. The structure is attached in its relaxed state to the surface of the blank with the exception of the overlap region, where the structure is not affixed. When subjected to a stretching force, the non-affixed region will stretch and therewith pull the two parts away from each other. The blank may also consist in two parts which are separated from each other by a gap of certain width when the parts are in a relaxed or non-loaded state. Only that part of the structure which extends over the gap (and is therewith not affixed) is permitted to stretch.

Thirdly, the blank can be made from any one of a variety of materials. Firstly, the blank as such can be omitted and the element comprised solely of the elastic structure 2, for instance in the form of a relatively fine-mesh net. The blank may also be made of elastic material which is capable of following partially the stretching and contracting movements of the structure. The blank may be comprised of nonwoven material, plastic, foam or like material. The blank will preferably be made from a vapour permeable material.

Fourthly, the opening or openings can be obtained in many different ways. The openings may have the form of discrete perforations in the blank or the form of a continuous slit which divides the blank into two parts over at least a part of its width. The slit may alternatively consist in intermittent slits, i.e. comprised of a plurality of mutually separated slits that are disposed in a straight line. The slit will conveniently extend transversely to the stretch direction of the blank, but may alternatively extend obliquely to this direction.

In some cases, the blank may consist in two separate parts which overlap over a given area. The opening need not necessarily be a through-aperture hole in the material. When an elastic net is mounted on the blank with the net held stretched longitudinally and transversely, pits will be formed in the blank at those locations where the meshes of the net contract. Such pits are able to fulfil the same function as typical "openings" when fastening the fastener means, by enclosing appropriately configured hooking devices.

The term "opening" as used here does not necessarily mean a slit or gap which has been preformed in the material. For instance, the "opening" may consist in a thinning of the blank material, with the thinned portions being marked in a manner that can be seen easily by the user. For instance, the blank may be provided with a tear line along which the blank is torn into different parts when pulling-out the free end of the blank, or where the blank is intended to be perforated by an appropriately configured hook device.

Some of the aforementioned variations will now be described in more detail with reference to the accompanying drawings.

Figure 4A:
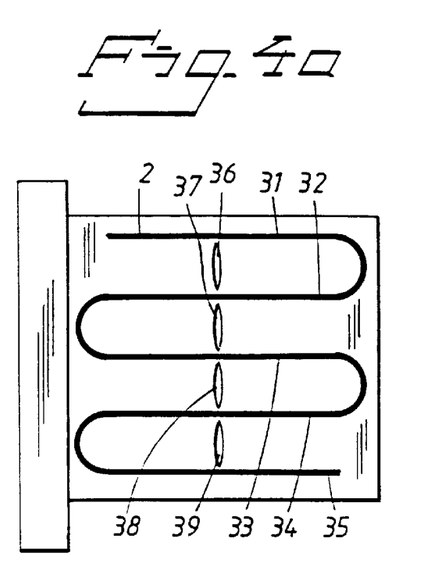
Figure 4B:
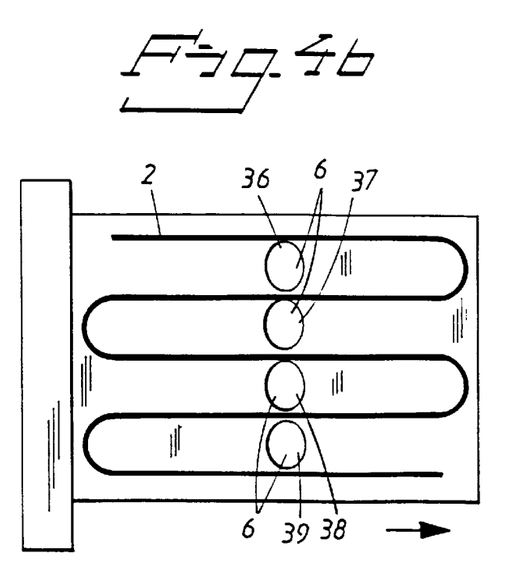

According to another embodiment of the first fastener element, as illustrated in FIGS. 4a, 4b, the element 1 is comprised of a rectangular nonwoven blank that has a fixed end 17 and a free end 18.

FIG. 4a shows the element in a relaxed state and FIG. 4b shows the same element in a stretched state. The blank is provided with a plurality of transversely extending buttonhole-like slits 36–39.

The elastic structure is comprised of a looped elastic thread loop 2 which includes a plurality of parallel segments 31–35 that extend between the slits 36–39. The loop 2 is able to stretch and contract in the direction of the parallel segments. The loop 2 is preferably in a stretched state when it is mounted on the blank.

The blank is compressed and the slits 36–39 therewith closed when no load acts on the loop 2, i.e. when the loop is relaxed. As the free end 18 of the blank is pulled in the stretch direction, as shown in FIG. 4b, the loop will be stretched and the slits 36–39 will widen in the direction of the pulling force. This will result in a gap in the blank. Oval shaped openings 6 are created in the gap, in the intervals between the parallel segments 31–35 of the loop 2. When the pulling force is released, the loop 2 will spring back to its relaxed state, therewith drawing the openings 6 together.

Figure 5A:
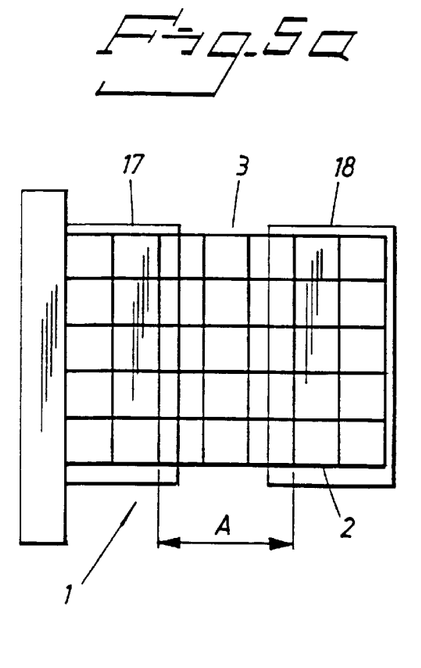
Figure 5B:
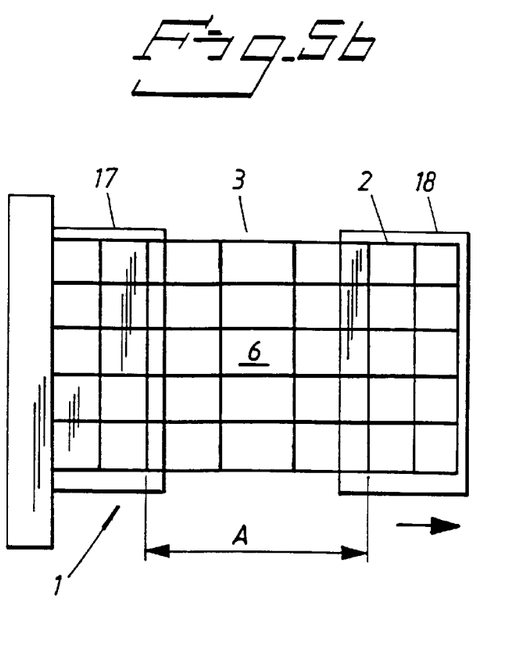

In the case of a third embodiment of the first fastener element 1, shown in FIGS. 5a, 5b, the element 1 is comprised of a rectangular nonwoven blank that has a fixed end 17 and a free end 18.

FIG. 5a shows the element in its relaxed state and FIG. 5b shows the element in its stretched state. The blank is divided by a broad slit 3 which either extends over the full width of the blank or over a major part thereof.

The elastic structure is comprised of an elastic net 2. The net 2 is attached to the blank, with the exception of a region A along the slit 3 at which the net 2 is not affixed to the blank. This free region A has a width which corresponds preferably to the width extension of one or more of the net meshes and extends across the slit 3. The net 2 is able to stretch and contract in all directions in the plane of the blank. When the free end 18 of the blank is pulled in the stretch direction, as shown in FIG. 5b, the aforesaid non-affixed region A of the net 2 will stretch so as to widen the slit 3 in the direction of the pulling force.

Figure 5C:
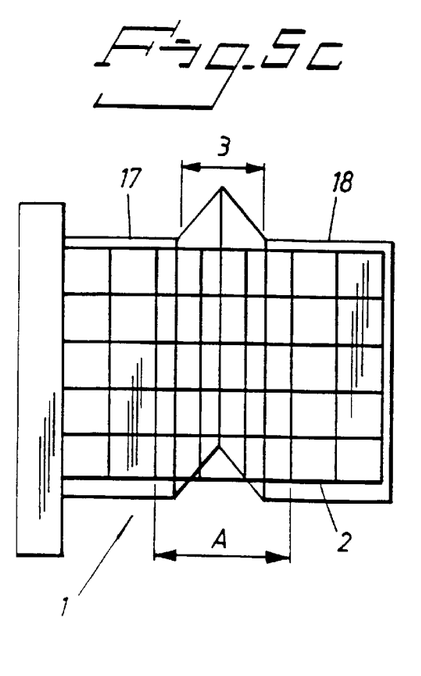
Figure 5D:
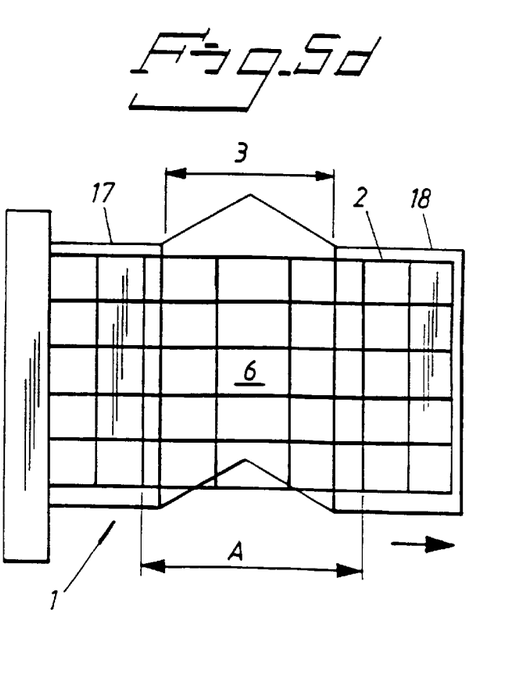

FIGS. 5c and 5d illustrate an alternative embodiment of a first fastener element 1 as illustrated in FIGS. 5a and 5b. In this case, the blank is not divided and is folded together over at least a part of the non-affixed region A. The blank is thus able to develop across the non-affixed region A, as the free end 18 of the blank is pulled-out.

In the case of a further embodiment (not shown), the net is mounted on the nonwoven material while stretched in at least the longitudinal direction of the net. The nonwoven material includes one or more openings, each of which is enclosed in a mesh. In the absence of load, i.e. in the absence of pulling forces on the net, the nonwoven material will be puckered or pleated due to the relaxed state of the net, and the openings will therefore be practically closed or at least drawn together. As the blank is pulled in its longitudinal direction, the net will stretch and the fibre material will smooth out. Those openings that are contained in the meshes will be widened in the stretch direction and will contract or draw together when the stretching force is released.

According to another embodiment (not shown), the first element is comprised of an elastic blank which is able to stretch and contract in at least the longitudinal direction of the blank. The blank may comprise a relatively fine-mesh net, and may optionally include larger meshes at certain chosen discrete regions. Alternatively, the blank may comprise perforated elastic material. As the blank is stretched, the meshes or the perforations, will widen in the stretch direction, and will re-close or contract when the force is released.

The design of the second element 4

The second element 4 is comprised generally of a flat, pliable blank provided with hook devices 5 made of a relatively stiff material and configured to fit into corresponding openings 6 in the first element when said element is stretched. Seen in general, the hook devices 5 shall be sufficiently small to enter respective widened openings 6 and sufficiently large to be retained in said openings in their closed or contracted state.

Figure 6A:
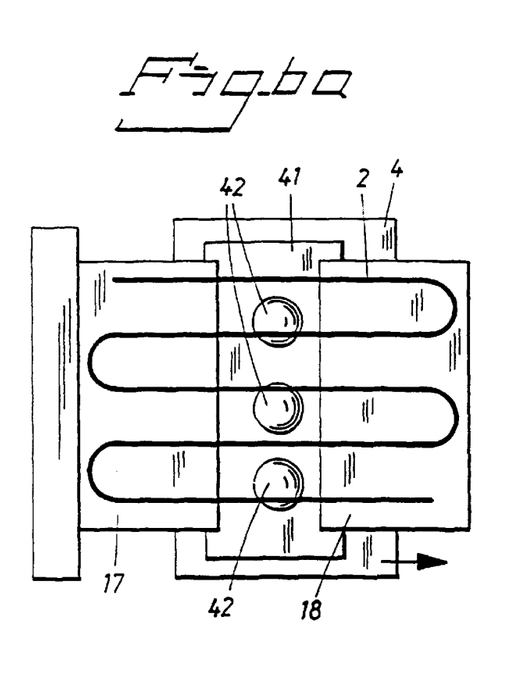
FIG. 6a shows the fastener means with the fastener elements not connected. The first element is shown in a stretched state with the opening widened. The arrows indicate the applied stretching forces.
Figure 6B:
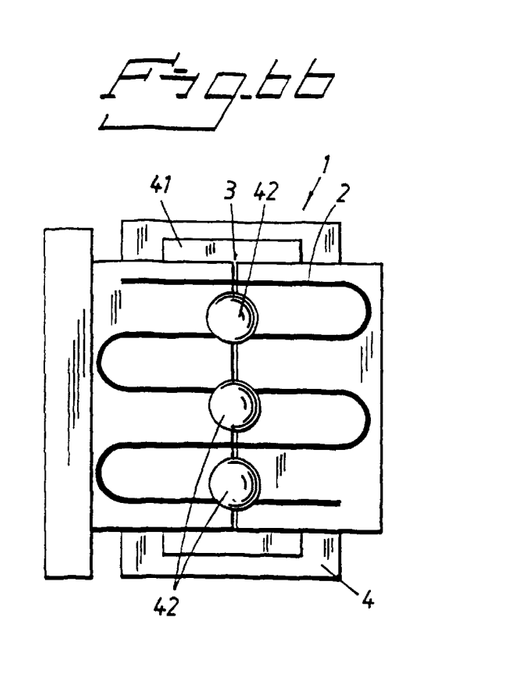
FIG. 6b shows the fastener means with the fastener elements connected. The first element springs back and the opening is drawn together around the hook devices. The arrows indicate the spring-back or contracting forces.

FIG. 6 illustrates an entire fastener means from above. The illustrated fastener means comprises a first fastener element 1 according to FIG. 3, and an underlying second fastener element 4. FIG. 6a shows the fastener means prior to being fastened, with the first element 1 stretched. FIG. 6b shows the fastener means in a closed state.

In the case of the FIG. 6 embodiment, the second element 4 is comprised of a flat, rectangular nonwoven blank which has mounted thereon a strip 41 of relatively rigid material, preferably a rigid plastic material. The strip carries hook devices in the form of upstanding, mushroom-like studs 42.

FIG. 7d illustrates the design of the studs. Each stud has a relatively short and narrow stem 43 which extends at right angles to the surface of the strip 41, and a broader, hemispherical head 44. The cross-sectional area of the head 44 is such as to enable the head to be inserted relatively easily in a corresponding opening 6, when said opening is widened. The size of the head 44, however, is much larger than the size of the opening 6 when the opening is closed, as evident from FIG. 6b.

Figure 8:
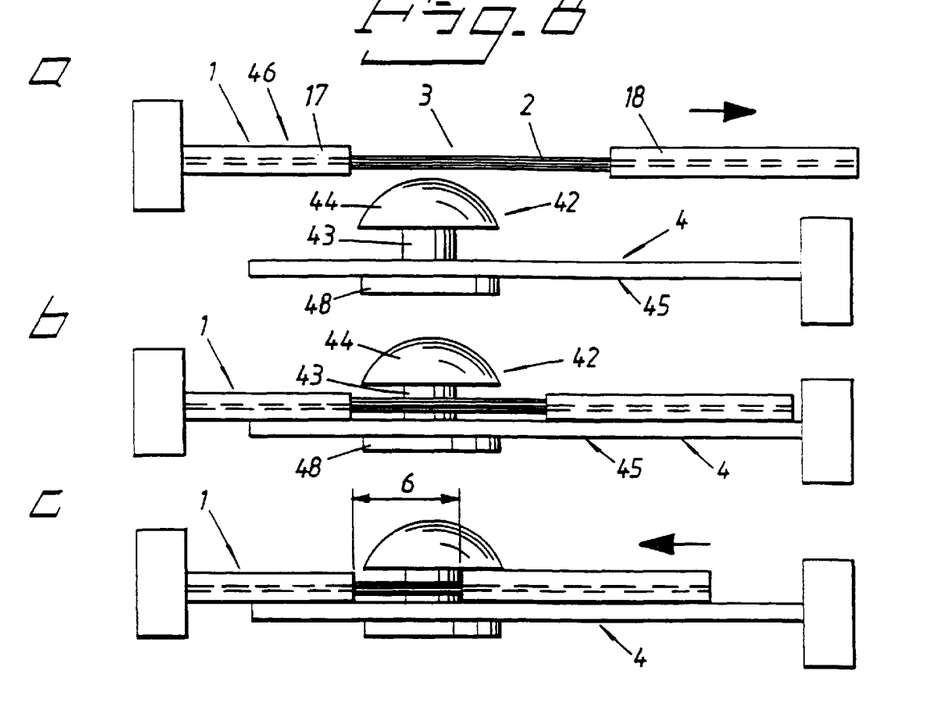
FIG. 8 illustrates an inventive fastener means from one side.

In the case of an embodiment illustrated in FIG. 8, the studs 42 are mounted on the blank 45. Each of the studs 42 is comprised generally of three parts, a base part 48, a stem 43 and a head 44. The stem 43 is held firmly in a hole in the blank 45.

FIG. 8a is a side view of an unfastened fastener means that includes a first fastener element 1, e.g., of the same type as that shown in FIG. 3. The first element 1 is comprised of a nonwoven blank 46 which has a fixed part 17 and a free 5 part 18. An elastic structure 2 is mounted along the full length of the blank 46 and joins the parts 17, 18 over a slit 3. The first element 1 is shown in a stretched state, with a pulling force acting on the free part 18 in the plane of the blank 46. The second element 4 is comprised of a nonwoven blank 45 fastened to the article. The blank 45 may be included in or form the front centre-region of the article.

FIG. 8b shows the same fastener means as the fastener is being fastened. The slit 3 is threaded over the head 44 of the hook device and the surfaces of the two blanks 45, 46 abut one another. The structure 2 is kept in its stretched state.

FIG. 8c illustrates the same fastener means after said means has been fastened. The slit 3 is drawn together over the stem 43 of the hook device. The two blanks 45, 46 are in mutual abutment. The structure 2 is allowed to spring back. The free part 18 of the blank 46 presses against one side of the stem 43. When the fastener means is in this state, it is not possible to loosen the first element 1 from the stud with a force that acts away from the plane of the blanks 45, 46, as the head 44 of the stud is much wider than the width of the contracted slit 3.

Design of the hook device

As will be seen from FIG. 8c, when the fastener means has been fastened, the stems 43 of respective studs will be subjected to a force which acts generally in the opposite direction to the stretch direction of the first element. The studs will therefore be constructed suitably to resist this force as effectively as possible.

Figure 7:
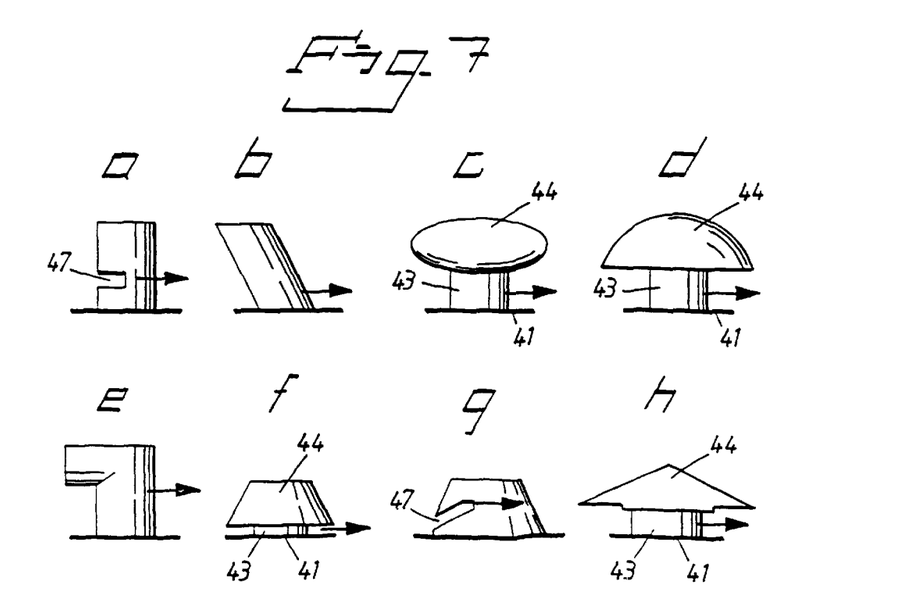
FIGS. 7a to 7h illustrate eight different embodiments of the hook device. The arrows indicate the direction in which the spring-back or contracted forces in the first element act on the hook device as the fastener means is fastened.

FIG. 7 shows eight possible variants of the design of the hook device, the arrows indicating the direction in which the major part of the forces can be thought to act on the studs while wearing the article.

The hook device illustrated in FIG. 7a has the form of an upstanding, generally cylindrical stud which defines a right angle in relation to the plane of the blank. Provided on the side of the stem is a notch or groove 47 in which the edge of the free part 18 of the first element (see FIG. 6a) can be held firmly after fastening the fastening means.

The hook device shown in FIG. 7b is an upstanding, generally cylindrical stud which defines an acute angle in relation to the plane of the blank. The stud is inclined to the direction of said force.

FIGS. 7c, 7d, 7f and 7h illustrate different mushroom-like studs which include a stem 43 and head 44. FIG. 7d shows one hook-like variant, while FIG. 7g shows a variant in which the groove 47 extends obliquely upwards.

The hook devices need not necessarily consist in outwardly projecting studs, but may have the form of conventional buttons, press studs, clamping holdfasts or corresponding devices. It is also conceivable to position the studs essentially in the plane of the blank 45 and to direct the studs against the direction of said force.

We claim:

1. A fastener for absorbent articles, such as pants-type diapers, diapers, and incontinence guards, said fastener comprising a first fastener element and a second fastener element which can be hooked together when donning the article, the first fastener element comprises at least one elastic part which is stretchable in a stretch direction and includes at least one opening, the opening is transversely directed in relation to the stretch direction of the elastic part; and the second fastener element includes at least one hook device being insertable through the opening when said opening is widened to a certain extent due to stretching of the elastic part, wherein contraction of the elastic part after such an insertion of the hook device causes the first and the second fastener elements to be mutually connected with the opening located around the hook device.

2. A fastener according to claim 1, wherein the first element comprises a sheet of pliable material; the opening has the form of a continuous slit in the sheet; the elastic part is comprised of a sheet-mounted elastic structure which can stretch at least transversely to the direction of the slit; and at least a part of the elastic structure extends transversely to the slit.

3. A fastener according to claim 2, wherein the elastic structure is comprised of at least one elastic loop which includes a number of generally parallel segments that can be stretched at least transversely to the direction of the slit and that extend transversely to said slit.

4. A fastener according to claim 2, wherein the elastic structure comprises an elastic net which can be stretched at least transversely to the direction of the slit.

5. A fastener according to claim 1, wherein the second fastener element is comprised of a generally flat blank and has relatively stiff hook devices upstanding from the plane of the blank; and each hook device has a bottom part located proximal to the surface of said blank and a top part which connects with said bottom part and which has a larger cross-sectional area than said bottom part.

6. A fastener according to claim 1, wherein the second fastener element is comprised of a generally flat blank and has hook devices which define an acute angle in relation to the plane of the blank and are much stiffer than the blank.

7. A fastener according to claim 1, wherein the second fastener element is comprised of a generally flat blank and has hook devices upstanding from the plane of the blank which are much stiffer than the blank; and each hook device includes a groove or notch for receiving parts around the opening.

8. A fastener according to claim 1, wherein at least a top part of the hook device has a cross-sectional area which is larger-than the size of the contracted opening.

9. A fastener according to claim 1, wherein the opening is a slit opening.

10. A fastener according to claim 1, wherein the opening is a gap opening.

11. A fastener according to claim 1, wherein the first element comprises a sheet of pliable material; the opening has the form of a number of intermittent slits in the sheet; the elastic part is comprised of a sheet-mounted elastic structure which can stretch at least transversely to the direction of the slit; and at least a part of the elastic structure extends transversely to the slit.

12. A fastener for absorbent articles, such as pants-type diapers, diapers, and incontinence guards, said fastener comprising a first fastener element and a second fastener element which can be hooked together when donning the article, the first fastener element includes at least one elastic part which is stretchable in a stretch direction and includes opening means transversely directed in relation to the stretch direction of the elastic part for receiving the second fastener element when said opening means is widened to a certain extent due to stretching of the elastic part;

the second fastener element includes at least one hook device insertable through the opening means; and said hook device including means for connecting with the first fastener element upon contraction of the elastic part after an insertion of the hook device in the opening means.

* * * * *